(12) United States Patent
Heckel et al.

(10) Patent No.: US 11,076,906 B2
(45) Date of Patent: *Aug. 3, 2021

(54) LOGARITHMIC AMPLIFIER, ELECTROSURGICAL GENERATOR INCLUDING SAME, AND METHOD OF CONTROLLING ELECTROSURGICAL GENERATOR USING SAME

(71) Applicant: COVIDIEN LP, Mansfield, MA (US)

(72) Inventors: Donald W. Heckel, Thornton, CO (US); Robert J. Behnke, II, Erie, CO (US)

(73) Assignee: Covidien LP, Mansfield, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/527,729

(22) Filed: Jul. 31, 2019

(65) Prior Publication Data

US 2019/0350637 A1 Nov. 21, 2019

Related U.S. Application Data

(62) Division of application No. 13/247,043, filed on Sep. 28, 2011, now Pat. No. 10,376,301.

(51) Int. Cl.
*A61B 18/12* (2006.01)
*A61B 18/00* (2006.01)

(52) U.S. Cl.
CPC ............ *A61B 18/1206* (2013.01); *A61B 2018/00642* (2013.01); *A61B 2018/00779* (2013.01);
(Continued)

(58) Field of Classification Search
CPC ........ A61B 18/1206; A61B 2018/0063; A61B 2018/00702; A61B 2018/00875;
(Continued)

(56) References Cited

U.S. PATENT DOCUMENTS 3,001,132 A 9/1961 Britt
4,429,694 A 2/1984 McGreevy
(Continued)

FOREIGN PATENT DOCUMENTS

DE 179607 C 11/1906
DE 390937 C 3/1924
(Continued)

OTHER PUBLICATIONS

International Search Report EP 07008207.8 dated Sep. 13, 2007.
(Continued)

*Primary Examiner* — Jon Eric C Morales
(74) *Attorney, Agent, or Firm* — Carter, DeLuca & Farrell LLP (57) ABSTRACT

An electrosurgical generator includes an RF output stage, a current sensor, a voltage sensor, first and second log amplifiers, and a controller. The RF output stage is configured to supply electrosurgical energy to tissue. The current sensor is configured to sense a current of the electrosurgical energy and generate a current signal corresponding to the current of the electrosurgical energy. The first log amplifier is configured to amplify and compress the current signal. The voltage sensor is configured to sense a voltage of the electrosurgical energy and generate a voltage signal in response thereto. The second log amplifier is configured to amplify and compress the voltage signal. The controller is configured to receive the amplified voltage signal and the amplified current signal and operatively control the generation of the electrosurgical energy as a function of the amplified voltage signal and the amplified current signal.

6 Claims, 5 Drawing Sheets

(52) U.S. Cl.
CPC .............. *A61B 2018/00827* (2013.01); *A61B 2018/00875* (2013.01); *A61B 2018/00892* (2013.01)

(58) Field of Classification Search
CPC . A61B 18/14; A61B 18/1442; A61B 18/1445; A61B 2018/00345; A61B 2018/00404; A61B 2018/00577; A61B 2018/00589; A61B 2018/00601; A61B 2018/00619; A61B 2018/00648; A61B 2018/00684; A61B 2018/0072; A61B 2018/00726; A61B 2018/0075; A61B 2018/00761; A61B 2018/00779; A61B 2018/00827; A61B 2018/00869; A61B 2018/00886; A61B 2018/00892; A61B 2018/126; A61B 2560/0238

See application file for complete search history.

(56) References Cited

U.S. PATENT DOCUMENTS

| | | | |
|---|---|---|---|
| 4,593,696 A | 6/1986 | Hochmair et al. |
| 4,750,488 A | 6/1988 | Wuchinich et al. |
| 4,754,757 A | 7/1988 | Feucht |
| 4,848,335 A | 7/1989 | Manes |
| 5,534,018 A | 7/1996 | Wahlstrand et al. |
| 6,270,497 B1 | 8/2001 | Sekino et al. |
| 6,507,758 B1 | 1/2003 | Greenberg et al. |
| D574,323 S | 8/2008 | Waaler |
| 8,617,154 B2 | 12/2013 | Johnston |
| 8,623,007 B2 | 1/2014 | Deborski et al. |
| 8,636,730 B2 | 1/2014 | Keppel |
| 8,641,712 B2 | 2/2014 | Couture |
| 8,668,690 B2 | 3/2014 | Couture |
| 8,745,846 B2 | 6/2014 | Behnke, II et al. |
| 8,944,834 B2 | 2/2015 | Plaven et al. |
| 8,968,293 B2 | 3/2015 | Gilbert |
| 8,968,297 B2 | 3/2015 | Collins |
| 9,023,025 B2 | 5/2015 | Behnke, II et al. |
| 9,028,479 B2 | 5/2015 | Orszulak |
| 9,028,481 B2 | 5/2015 | Behnke, II |
| 9,033,970 B2 | 5/2015 | Behnke, II et al. |
| 9,033,973 B2 | 5/2015 | Krapohl et al. |
| 9,039,692 B2 | 5/2015 | Behnke, II et al. |
| 9,039,693 B2 | 5/2015 | Behnke, II et al. |
| 9,050,089 B2 | 6/2015 | Orszulak |
| 9,099,863 B2 | 8/2015 | Smith et al. |
| 9,192,422 B2 | 11/2015 | Collins |
| 9,265,560 B2 | 2/2016 | Johnston |
| 9,375,247 B2 | 6/2016 | Orszulak et al. |
| 9,539,050 B2 | 1/2017 | Podhajsky |
| 9,844,404 B2 * | 12/2017 | Behnke, II ............. A61B 18/14 |
| 10,376,301 B2 * | 8/2019 | Heckel ............... A61B 18/1206 |
| 2004/0100325 A1 | 5/2004 | van Amerom |
| 2004/0167508 A1 | 8/2004 | Wham et al. |
| 2005/0195037 A1 | 9/2005 | Dupuis et al. |
| 2007/0082627 A1 | 4/2007 | Church |
| 2008/0036399 A1 | 2/2008 | Olson et al. |
| 2008/0082098 A1 | 4/2008 | Tanaka et al. |
| 2009/0157067 A1 | 6/2009 | Kane et al. |
| 2009/0171342 A1 | 7/2009 | Klimovitch et al. |
| 2010/0010480 A1 | 1/2010 | Mehta et al. |
| 2011/0213355 A1 | 9/2011 | Behnke, II |
| 2012/0022521 A1 | 1/2012 | Odom et al. |
| 2012/0136348 A1 | 5/2012 | Condie et al. |
| 2012/0239020 A1 | 9/2012 | Cunningham |
| 2012/0239025 A1 | 9/2012 | Smith |
| 2013/0079763 A1 | 3/2013 | Heckel et al. |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2602517 A1 | 7/1976 |
| DE | 2504280 A1 | 8/1976 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 3904558 A1 | 8/1990 |
| DE | 3942998 A1 | 7/1991 |
| DE | 4206433 A1 | 9/1993 |
| DE | 4339049 A1 | 5/1995 |
| DE | 19506363 A1 | 8/1996 |
| DE | 19717411 A1 | 11/1998 |
| DE | 19848540 A1 | 5/2000 |
| EP | 0246350 A1 | 11/1987 |
| EP | 0267403 A2 | 5/1988 |
| EP | 0296777 A2 | 12/1988 |
| EP | 0310431 A2 | 4/1989 |
| EP | 0325456 A2 | 7/1989 |
| EP | 0336742 A2 | 10/1989 |
| EP | 0390937 A1 | 10/1990 |
| EP | 0422594 A1 | 4/1991 |
| EP | 0556705 A1 | 8/1993 |
| EP | 0608609 A2 | 8/1994 |
| EP | 0836868 A2 | 4/1998 |
| EP | 0880220 A2 | 11/1998 |
| EP | 0882955 A1 | 12/1998 |
| EP | 1051948 A2 | 11/2000 |
| EP | 1366724 A1 | 12/2003 |
| EP | 1776929 A1 | 4/2007 |
| EP | 1905371 A1 | 4/2008 |
| FR | 1275415 A | 11/1961 |
| FR | 1347865 A | 1/1964 |
| FR | 2313708 A1 | 12/1976 |
| FR | 2364461 A1 | 4/1978 |
| FR | 2502935 A1 | 10/1982 |
| FR | 2517953 A1 | 6/1983 |
| FR | 2573301 A1 | 5/1986 |
| SU | 166452 | 11/1964 |
| SU | 698674 A1 | 11/1979 |
| SU | 727201 A2 | 4/1980 |
| WO | 0211634 | 2/2002 |
| WO | 0245589 | 6/2002 |
| WO | 03090635 A1 | 11/2003 |
| WO | 2006050888 A1 | 5/2006 |
| WO | 2008053532 A1 | 5/2008 |

OTHER PUBLICATIONS

International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Feb. 25, 2009.
International Search Report EP08015601.1 dated Dec. 5, 2008.
International Search Report EP08155780 dated Jan. 19, 2009.
International Search Report EP08016540.0 dated Feb. 25, 2009.
International Search Report EP08166208.2 dated Dec. 1, 2008.
International Search Report EP09003678.1 dated Aug. 7, 2009.
International Search Report EP09004250.8 dated Aug. 2, 2010.
International Search Report EP09005160.8 dated Aug. 27, 2009.
International Search Report EP09009860 dated Dec. 8, 2009.
International Search Report EP09012386 dated Apr. 1, 2010.
International Search Report EP09012388.6 dated Apr. 13, 2010.

(56) References Cited

OTHER PUBLICATIONS

International Search Report EP09012389.4 dated Jul. 6, 2010.
International Search Report EP09012391.0 dated Apr. 19, 2010.
International Search Report EP09012392 dated Mar. 30, 2010.
International Search Report EP09012396 dated Apr. 7, 2010.
International Search Report EP09012400 dated Apr. 7, 2010.
International Search Report EP09156861.8 dated Jul. 14, 2009.
International Search Report EP09158915 dated Jul. 14, 2009.
International Search Report EP09164754.5 dated Aug. 21, 2009.
International Search Report EP09169377.0 dated Dec. 15, 2009.
International Search Report EP09169588.2 dated Mar. 2, 2010.
International Search Report EP09169589.0 dated Mar. 2, 2010.
International Search Report EP09172749.5 dated Dec. 4, 2009.
International Search Report EP10001808.4 dated Jun. 21, 2010.
International Search Report EP10150563.4 dated Jun. 10, 2010.
International Search Report EP10150564.2 dated Mar. 29, 2010.
International Search Report EP10150565.9 dated Mar. 12, 2010.
International Search Report EP10150566.7 dated Jun. 10, 2010.
International Search Report EP10150567.5 dated Jun. 10, 2010.
International Search Report EP10164740.2 dated Aug. 3, 2010.
International Search Report EP10171787.4 dated Nov. 18, 2010.
International Search Report EP10172636.2 dated Dec. 6, 2010.
International Search Report EP10174476.1 dated Nov. 12, 2010.
International Search Report EP10178287.8 dated Dec. 14, 2010.
International Search Report EP10179321.4 dated Mar. 18, 2011.
International Search Report EP10179353.7 dated Dec. 21, 2010.
International Search Report EP10179363.6 dated Jan. 12, 2011.
International Search Report EP10180004.3 dated Jan. 5, 2011.
International Search Report EP10180964.8 dated Dec. 22, 2010.
International Search Report EP10180965.5 dated Jan. 26, 2011.
International Search Report EP10181018.2 dated Jan. 26, 2011.
U.S. Appl. No. 10/406,690 to Robert J. Behnke, II, filed Apr. 3, 2003, abandoned.
U.S. Appl. No. 10/573,713 to Robert H. Wham, filed Mar. 28, 2006, abandoned.
U.S. Appl. No. 11/242,458 to Daniel J. Becker, filed Oct. 3, 2005, abandoned.
Wald et al., "Accidental Burns", JAMA, Aug. 16, 1971, vol. 217, No. 7, pp. 916-921.
Vallfors et al., "Automatically Controlled Bipolar Electrosoagulation—'COA-COMP'", Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Prutchi et al. "Design and Development of Medical Electronic Instrumentation", John Wiley & Sons, Inc. 2005.
Muller et al. "Extended Left Hemicolectomy Using the LigaSure Vessel Sealing System", Innovations That Work; Company Newsletter; Sep. 1999.
Ogden Goertzel Alternative to the Fourier Transform: Jun. 1993 pp. 485-487, Electronics World; Reed Business Publishing, Sutton, Surrey, BG vol. 99, No. 9. 1687.
Hadley I C D et al., "Inexpensive Digital Thermometer for Measurements on Semiconductors", International Journal of Electronics; Taylor and Francis. Ltd.; London, GB; vol. 70, No. 6 Jun. 1, 1991; pp. 1155-1162.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Richard Wolf Medical Instruments Corp. Brochure, "Kleppinger Bipolar Forceps & Bipolar Generator", 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy", Journal Neurosurgery, 83; (1995) pp. 271-276.
Geddes et al.. "The Measurement of Physiologic Events by Electrical Impedence" Am. J. MI, Jan. Mar. 1964, pp. 16-27.

Cosman et al., "Methods of Making Nervous System Lesions", In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994), pp. 297-307.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Cosman et al., "Radiofrequency Lesion Generation and Its Effect on Tissue Impedance", Applied Neurophysiology 51: (1988) pp. 230-242.
Ni W. et al. "A Signal Processing Method for the Coriolis Mass Flowmeter Based on a Normalized . . . " Journal of Applied Sciences—Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297, Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone", Neurosurgery 15: (1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300", 1 p. Sep. 1998.
Valleylab Brochure "Valleylab Electroshield Monitoring System", 2 pp. Nov. 1995.
International Search Report EP 98300964.8 dated Dec. 4, 2000.
International Search Report EP 04009964 dated Jul. 13, 2004.
International Search Report EP 04011375 dated Sep. 10, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001484.0 dated Jun. 14, 2010.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001494.9 dated Aug. 25, 2010.
International Search Report EP 07001494.9 extended dated Mar. 7, 2011.
International Search Report EP 07001527.6 dated May 9, 2007.
International Search Report EP 07004355.9 dated May 21, 2007.
International Search Report EP10181060.4 dated Jan. 26, 2011.
International Search Report EP10182003.3 dated Dec. 28, 2010.
International Search Report EP10182005.8 dated Jan. 5, 2011.
International Search Report EP10188190.2 dated Nov. 22, 2010.
International Search Report EP10191319.2 dated Feb. 22, 2011.
International Search Report EP10195393.3 dated Apr. 11, 2011.
International Search Report EP11155959.7 dated Jun. 30, 2011.
International Search Report EP11155960.5 dated Jun. 10, 2011.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.
International Search Report PCT/US04/13443 dated Dec. 10, 2004.
International Search Report PCT/US08/052460 dated Apr. 24, 2008.

(56) References Cited

OTHER PUBLICATIONS

International Search Report PCT/US09/46870 dated Jul. 21, 2009.
European Search Report issued in corresponding patent application No. EP 12 18 6066 dated Mar. 4, 2011.

* cited by examiner

LOGARITHMIC AMPLIFIER, ELECTROSURGICAL GENERATOR INCLUDING SAME, AND METHOD OF CONTROLLING ELECTROSURGICAL GENERATOR USING SAME

CROSS REFERENCE TO RELATED APPLICATION

The present application a divisional application of U.S. patent application Ser. No. 13/247,043, filed on Sep. 28, 2011, the entire contents of which are incorporated herein by reference.

BACKGROUND

1. Technical Field

The present disclosure relates to electrosurgery. More particularly, the present disclosure relates to a logarithmic amplifier, an electrosurgical generator including the same, and a method of controlling an electrosurgical generator using the same.

2. Discussion of Related Art

Electrosurgery is the application of electricity and/or electromagnetic energy to cut, dissect, ablate, coagulate, cauterize, seal or otherwise treat biological tissue during a surgical procedure. Generally, electrosurgery utilizes an electrosurgical generator operable to output energy and active and return electrodes that are electrically connected via a cable assembly to the generator. The electrosurgical generator generates an electromagnetic wave (referred to herein as "electrosurgical energy"), typically above 100 kilohertz, between the active and return electrodes when applied to tissue. The electromagnetic wave created therebetween dissipates energy as heat as it travels between the electrodes. The electrosurgical energy usually has a frequency above 100 kilohertz to avoid muscle and/or nerve stimulation.

During electrosurgery, current generated by the electrosurgical generator is conducted through the patient's tissue disposed between the two electrodes. The current causes the tissue to heat up as the electromagnetic wave overcomes the tissue's impedance. Although many other variables affect the total heating of the tissue, usually more current density correlates to increased heating.

A variety of types of instruments utilizing electromagnetic radiation have been employed for various types of monopolar and bipolar electrosurgery. The basic purpose of both monopolar and bipolar electrosurgery is to produce heat to achieve the desired tissue/clinical effect. In monopolar electrosurgery, devices use an instrument with a single, active electrode to deliver energy from an electrosurgical generator to tissue, and a patient return electrode or pad that is attached externally to the patient (e.g., a plate positioned on the patient's thigh or back) as the means to complete the electrical circuit between the electrosurgical generator and the patient. When the electrosurgical energy is applied, the energy travels from the active electrode, to the surgical site, through the patient and to the return electrode. In bipolar electrosurgery, both the active electrode and return electrode functions are performed at the site of surgery. Bipolar electrosurgical devices include two electrodes that are located in proximity to one another for the application of current between their surfaces. Bipolar electrosurgical current travels from one electrode, through the intervening tissue to the other electrode to complete the electrical circuit. Bipolar instruments generally include end-effectors, such as grippers, cutters, forceps, dissectors and the like.

Electrosurgical generators apply various currents, voltages and frequencies to achieve various tissue effects. The current, voltage, and frequency may be varied to achieve a target tissue impedance, a target power, a target voltage, and the like. These target values are generally based upon the surgical procedure to be performed, tissue characteristics, and/or the desired tissue/clinical effect. Electrosurgical generators employ one or more control systems to achieve these target values and to prevent the electrosurgical generator from operating outside predetermined constraints.

SUMMARY

Electromagnetic energy is generally classified by increasing energy or decreasing wavelength into radio waves, microwaves, infrared, visible light, ultraviolet, X-rays and gamma-rays. As it is used in this description, "transmission line" generally refers to any transmission medium that can be used for the propagation of signals from one point to another.

Although the following description describes the use of logarithmic amplifiers to compress a large output range of a generator to a small feedback range, the teachings of the present disclosure may also apply to a variety of applications where signals of large dynamic range may be encountered.

According to an aspect, a control system for controlling a generator is provided. The control system includes a sensor, a log amplifier, and a controller. The sensor generates a sensor signal. The sensor may be a voltage sensor or a current sensor. The log amplifier is coupled to the sensor and amplifies the sensor signal. The controller generates an output signal as a function of the amplified sensor signal. In some aspects, the control system further includes a summer to sum a setpoint and the negation of the amplified signal from the log amplifier. The controller may be adapted to generate electrosurgical energy, i.e., the output signal may be electrosurgical energy. The generator may be an electrosurgical generator. The electrosurgical generator may be a portable electrosurgical generator coupled to a portable surgical instrument. In other embodiments, the generator may be an ultrasonic generator or a microwave generator.

In any of the aspects, the control system includes a summer. The summer sums a setpoint and a negation of the amplified signal from the log amplifier to generate an error. The controller may generate the output signal as a function of the error.

In any of the aspects, the control system includes a voltage sensor having a plurality of capacitors. The plurality of capacitors forms a voltage divider network that is in electrical communication with the output signal. The sensor signal may be a voltage of a capacitor of the divider network.

According to another aspect of the present disclosure, the controller is a proportional-integral-derivative controller. The proportional-integral-derivative controller may have one or more variable gain coefficients. The proportional-integral-derivative controller can vary a proportional gain coefficient, an integral gain coefficient, and a derivative gain coefficient. One or more gain coefficients may be varied as a function of the amplified sensor signal. The controller may convert the amplified sensor signal to an RMS value or to an antilog of the amplified sensor signal.

In any of the aspects, an electrosurgical generator includes an RF output stage, a current sensor, first and second log amplifiers, a voltage sensor and a controller. The RF output stage supplies electrosurgical energy to tissue. The current sensor senses a current of the electrosurgical energy. The voltage sensor senses a voltage of the electrosurgical energy. The first log amplifier amplifies the current signal. The second log amplifier amplifiers the voltage signal. The controller receives the amplified voltage and current signals. The controller may be configured to control the generation of the electrosurgical energy as a function of the amplified voltage signal and/or the amplified current signal.

In any of the aspects, the controller may be configured to calculate the sum of a log voltage signal and a log current signal to compute a measured log power. The controller may be further configured to compare the measured log power against a target log power to compute an error signal.

In any of the aspects, the electrosurgical generator may include a plurality of capacitors forming a capacitor divider network coupled to the RF output stage for measuring voltage of the electrosurgical energy.

In any of the aspects, voltage sensor may include a plurality of capacitors that form a capacitor divider network. The capacitor divider network is in electrical communication with the electrosurgical energy. Additionally or alternatively, the capacitor divider network may be coupled to the RF output stage.

In any of the aspects, the electrosurgical generator may include a dual directional coupler adapted for measurement of forward and reflective voltage.

In any of the aspects, the controller is a proportional-integral-derivative controller. The proportional-integral-derivative controller may employ one or more variable gain coefficients. The proportional-integral-derivative controller may be configured to vary a proportional gain coefficient, an integral gain coefficient, and/or a derivative gain coefficient. The proportional-integral-derivative controller may include one or more look-up tables to vary one or more gain coefficients. One or more gain coefficients may be determined using an affine algorithm. In any of the aspects, a measured log power may be compared against a target log power to compute an error signal used by the proportional-integral-derivative controller.

In any of the aspects, a gain coefficient may be varied as a function of the amplified voltage signal and/or the amplified current signal. The proportional-integral-derivative controller may have a setpoint of log power, log impedance, log current, or log voltage. The controller may be configured to calculate the log power by adding the amplified log current signal to the amplified log voltage signal. The controller may be configured to calculate log impedance by subtracting the amplified log current signal from the amplified log voltage signal. The electrosurgical generator may operate without calculating an antilog, e.g., the gain coefficients may change based upon a log power or a log impedance.

According to an aspect of the present disclosure, a method of controlling an electrosurgical generator is provided. The method includes the initial steps of supplying electrosurgical energy to tissue, determining a current of the electrosurgical energy, and determining a log of the determined current of the electrosurgical energy, determining a voltage of the electrosurgical energy. The method further includes the steps of determining a log of the determined voltage of the electrosurgical energy, and controlling the electrosurgical energy as a function of the log of the determined current and the log of the determined voltage.

The method may further include the steps of applying a proportional-integral-derivative transfer function using the log of the determined current, the log of the determined voltage, a log impedance, and/or a log power. The method may further include the steps of adjusting the electrosurgical energy as a function of the applied proportional-integral-derivative transfer function, and adjusting a gain coefficient of the proportional-integral-derivative transfer function. The proportional-integral-derivative transfer function may be applied to a comparison between a setpoint and one of the log of the determined current, the log of the determined voltage, the log impedance, and the log power (e.g., feedback is subtracted from the setpoint to provide an error signal).

BRIEF DESCRIPTION OF THE DRAWINGS

Objects and features of the presently-disclosed logarithmic amplifier, electrosurgical generator including the same, and a method of controlling an electrosurgical generator using the same will become apparent to those of ordinary skill in the art when descriptions of various embodiments thereof are read with reference to the accompanying drawings, of which.

DETAILED DESCRIPTION

Hereinafter, embodiments of a logarithmic amplifier, an electrosurgical generator including the same, and a method of controlling an electrosurgical generator using the same of the present disclosure are described with reference to the accompanying drawings. Like reference numerals may refer to similar or identical elements throughout the description of the figures. In the following description, well-known functions or constructions are not described in detail to avoid obscuring the present disclosure in unnecessary detail.

Various embodiments of the presently-disclosed logarithmic amplifier are suitable for use in electrosurgical generators and electrosurgical systems including the same. The presently-disclosed logarithmic (log) amplifier embodiments can be used to amplify and compress a signal which varies over a large dynamic range into a suitable log amplifier output range, e.g., 0 volts to about 3 volts.

Figure 1:
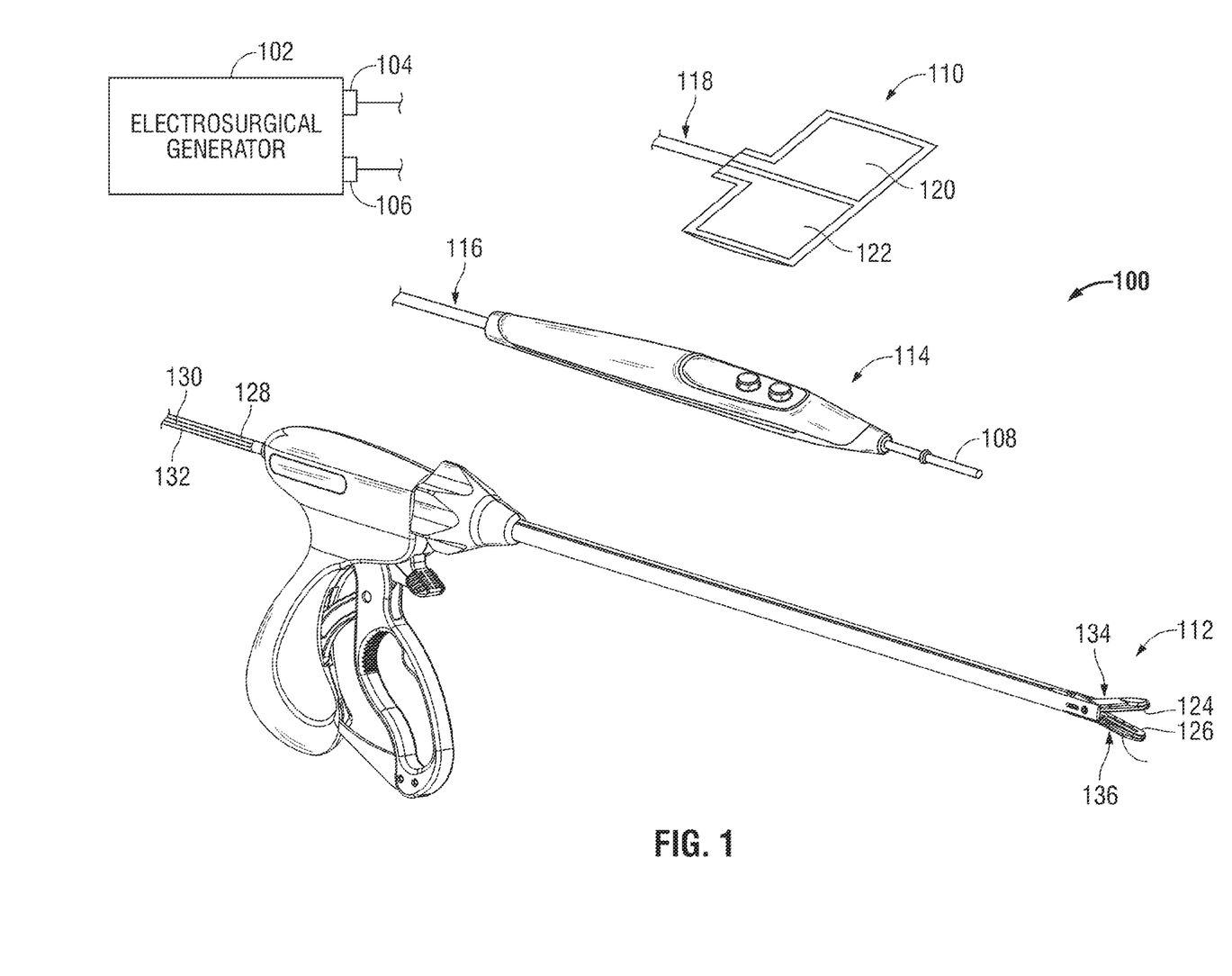
FIG. 1 shows an illustration of an electrosurgical system having an electrosurgical generator that uses logarithmic amplifiers in accordance with an embodiment of the present disclosure.

FIG. 1 shows an illustration of a bipolar and monopolar electrosurgical system 100 in accordance with an embodiment of the present disclosure. The electrosurgical system 100 includes a generator 102 that uses one or more logarithmic amplifiers (described below).

In some embodiments, the generator 102 is an electrosurgical generator adapted to supply electrosurgical energy to tissue, e.g., to meet the needs of the surgeon or surgical team for hospital, surgery center, and/or office-based procedures. The generator 102 may be adapted for use to perform monopolar and/or bipolar electrosurgical procedures including vessel-sealing procedures and/or other procedures. The generator 102 may include a plurality of outputs (e.g., terminals 104 and 106) for interfacing with various electrosurgical instruments (e.g., a monopolar active electrode 108, a return pad 110, bipolar electrosurgical forceps 112, a footswitch (not shown), etc.). The generator 102 may additionally, or alternatively, include electronic circuitry that is configured to generate radio-frequency power (or other type of surgical energy, e.g., light energy, microwave energy, ultrasonic energy, etc.) specifically suited for various electrosurgical modes (e.g., cutting, blending, division, etc.) and procedures (e.g., monopolar treatment, bipolar treatment, vessel sealing, etc.). The generator 102 may have a power range. In some embodiments, the generator 102 may have a power range from about 1 milliwatt (mW) ($1 \times 10^{-3}$ watts) to about 150 kilowatts (kW) ($1 \times 10^3$ watts).

The system 100 includes a monopolar electrosurgical instrument 114 having one or more electrodes 108 for treating tissue of a patient (e.g., electrosurgical pencil, electrosurgical cutting probe, ablation electrode(s), etc.). Electrosurgical RF energy is supplied to the instrument 114 by the generator 102 via a transmission line, e.g., supply line 116. As mentioned above, "transmission line" generally refers to any transmission medium that can be used for the propagation of signals from one point to another. Supply line 116 is operably connected to an active terminal 104 of the generator 102, allowing the instrument 114 to coagulate, ablate, or otherwise treat tissue. The energy is returned from electrode 108 through tissue to the generator 102 via a transmission line, e.g., via a return line 118 of the return pad 110, at a return terminal 106 of the generator 102. The active terminal 104 and the return terminal 106 may include connectors (not shown) configured to interface with plugs (not shown) of the instrument 114 and the return electrode 110, which are disposed at the ends of the supply line 116 and the return line 118, respectively.

The system 100 includes return electrodes 120, 122 within return pad 110 that are arranged to minimize the chances of tissue damage by maximizing the overall contact area with the patient's tissue. The generator 102 and the return electrode 110 may additionally, or alternatively, be configured for monitoring contact quality to ensure that sufficient contact exists therebetween to further minimize chances of tissue damage.

The system 100 generally includes a bipolar electrosurgical forceps instrument 112 having one or more electrodes (e.g., electrodes 124 and 126) for treating tissue of a patient. In some embodiments, as shown in FIG. 1, the instrument 112 includes opposing jaw members 134, 136 having an active electrode 124 and a return electrode 126 disposed therein, respectively. The active electrode 124 and the return electrode 126 are connectable to the generator 102 through a transmission line 128, e.g., a cable that includes a supply line 130 and a return line 132 coupled to the active terminal 104 and the return terminal 106, respectively. The instrument 112 is coupled to the generator 102 at a connector having connections to the active terminal 104 and the return terminal 106 (e.g., pins) via a plug (not shown) disposed at the end of the transmission line 128, wherein the plug includes contacts from the supply line 130 and the return line 132.

The generator 102 may be any suitable type (e.g., electrosurgical, microwave, etc.) and may include a plurality of connectors to accommodate various types of electrosurgical instruments (e.g., instrument 114, electrosurgical forceps 112, etc.). The generator 102 may be configured to operate in a variety of modes such as ablation, monopolar and bipolar cutting, coagulation, and other modes. The generator 102 may include a switching mechanism (e.g., relays) to switch the supply of energy, e.g., RF energy, between the connectors, such that, for instance, when the instrument 114 is connected to the generator 102, only the monopolar plug receives RF energy. The active terminal 104 and return terminals 106 may be coupled to a plurality of connectors (e.g., inputs and outputs) of the generator 102 to power a variety of instruments.

The generator 102 may include a user interface, e.g., configured to provide user-input capabilities and/or capabilities for simplified use and/or programming of the generator 102. The generator 102 includes suitable input controls (e.g., buttons, activators, switches, touch screen and the like) adapted to enable a user to selectively configure one or more operating parameters of the generator 102, or component thereof, e.g., depending upon a particular purpose and/or to achieve a desired surgical outcome. In addition, the generator 102 may include one or more display screens, such as a flat-panel display, e.g., an LCD (liquid crystal display), plasma display panel (PDP), organic light emitting diode (OLED), or electro-luminescent display (ELD), for providing the user with a variety of output information (e.g., intensity settings, treatment complete indicators, etc.). The controls allow the user to adjust power of the RF energy, waveform, and/or other parameters to achieve the desired waveform suitable for a particular task (e.g., coagulating, tissue sealing, intensity setting, etc.). The instruments 112, 114 may also include a plurality of input controls that may be redundant with certain input controls of the generator 102. Placing the input controls at the instruments 112, 114 allows for easier and faster modification of RF energy parameters during the surgical procedure without requiring user interaction with the generator 102.

Figure 2:
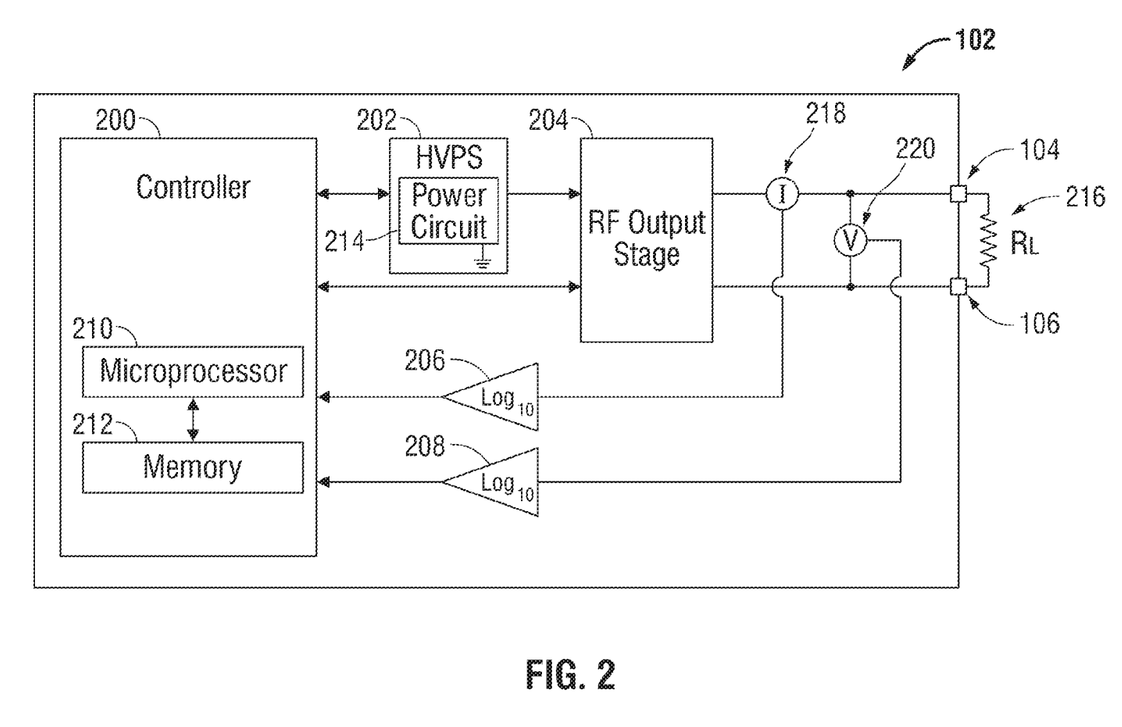
FIG. 2 shows a block diagram of the electrosurgical generator of FIG. 1 that uses logarithmic amplifiers in accordance with an embodiment of the present disclosure.

Referring to the drawings, FIG. 2 shows a block diagram of the electrosurgical generator 102 of FIG. 1 in accordance with an embodiment of the present disclosure. Electrosurgical generator 102 includes a controller 200, a high-voltage power supply 202 (HVPS), a radio-frequency (RF) output stage 204, and log amplifiers 206, 208. The controller 200 includes a processor unit 210 and a memory 212. The processor unit 210 may include any type of computing device, computational circuit, or any type of processor or processing circuit capable of executing a series of instructions that are stored in a computer-readable storage medium (e.g., memory 212), which may be any device or medium that can store code and/or data. In some embodiments, the processor unit 210 may be any suitable microcontroller, microprocessor (e.g., Harvard or Von Neumann architectures), PLD, PLA, or other suitable digital logic. In some embodiments, the memory 212 may be volatile, non-volatile, solid state, magnetic, or other non-transitory computer-readable medium.

The controller 200 may include various circuitry (e.g., amplifiers, buffers, and the like) to interface the processor unit 210 to circuitry within the electrosurgical generator 102. The controller 200 receives various feedback signals that are analyzed by the processor unit 210 to provide control signals in response thereto. The control signals from the controller 200 control the HVPS 202 and the RF output stage 204 to provide electrosurgical energy to tissue, which is represented by a load $R_L$ 216.

The HVPS 202 includes a power circuit 214. The power circuit 214 supplies a suitable electric current to the RF output stage 204. The RF output stage 204 converts the current from the power circuit 214 to electrosurgical energy for application to the load $R_L$ 216. In some embodiments, the HVPS 202 provides a DC signal to the RF output stage 204, which, in turn, generates the electrosurgical energy using a push-pull transistor configuration coupled to a primary side of a step-up transformer (not shown).

As previously mentioned, the controller 200 receives feedback from various feedback signals that are analyzed by the processor unit 210 to provide control signals in response thereto. The controller 200 may receive a log current from the log amplifier 206 and/or a log voltage from the log amplifier 208. In some embodiments, the controller 200 receives a current signal from a current sensor 218 after amplification by the log amplifier 206. The controller 200 may additionally, or alternatively, receive a voltage signal from a voltage sensor 220 after amplification by the log amplifier 208.

Log amplifiers 206, 208 may be log amplifiers that saturate with negative input, and/or may be output polarity independent of input polarity (e.g., a detecting log amp). Log amplifiers 206, 208 may additionally, or alternatively, be true log amplifiers (e.g., may have a symmetrical response to positive or negative signals). Additionally or alternatively, the log amplifiers 206 and 208 may be successive detection log amplifiers.

The controller 200 receives the log current and log voltage signals from log amplifiers 206 and 208, respectively, and controls the high-voltage power supply 202 in response thereto. In some embodiments, the controller 200 may be a proportional-integral-derivative controller ("PID controller").

The controller 200 may be adapted to control the output of the electrosurgical generator 102 to achieve a target log voltage, a target log current, a target power, a target log power, and/or a target log impedance, e.g., a target log tissue impedance. The controller 200 may be configured to calculate log power by adding the amplified log current signal from the log amplifier 206 to the amplified log voltage signal from the log amplifier 208. The controller 200 may be configured to calculate the log impedance by subtracting the log current signal received from the log amplifier 206 from the log voltage signal received from the log amplifier 208. In some embodiments of the present disclosure, the controller 200 converts an amplified signal from the log amplifier 206 and/or the log amplifier 208 to an RMS value or an antilog of the amplified sensor signal. In other embodiments of the present disclosure, the controller 200 does not calculate an antilog of either of the signals from the log amplifier 206 or the log amplifier 208.

The controller 200 may have one or more variable gain coefficients, e.g., a PID controller may vary one or more of a proportional gain coefficient, an integral gain coefficient, or an integral gain coefficient. In some embodiments, the one or more coefficients may be varied based upon a log current, a log voltage, a log impedance, and/or a log power.

Figure 3:
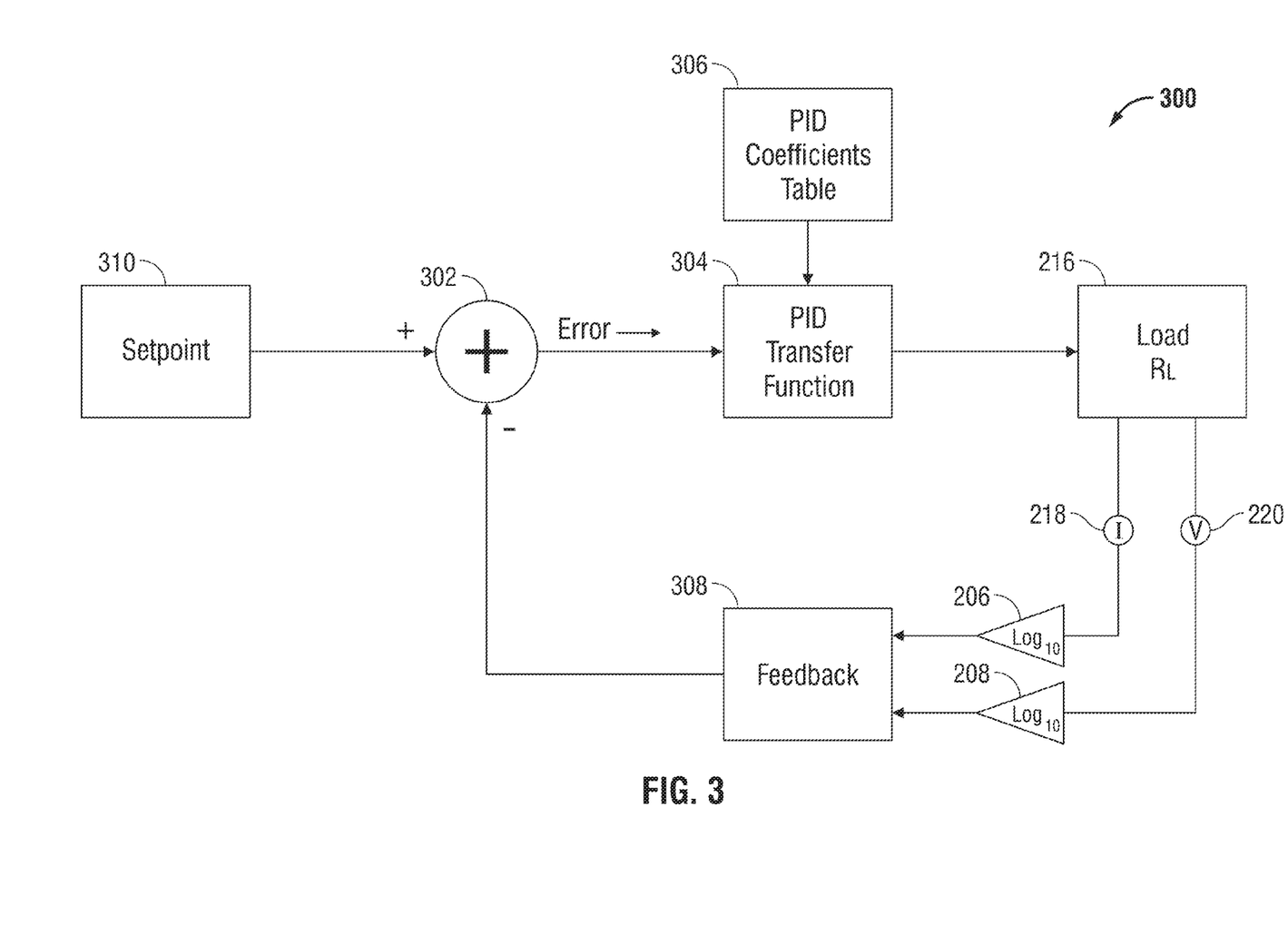
FIG. 3 shows a block diagram of the control system of the electrosurgical generator of FIG. 2 in accordance with an embodiment of the present disclosure.

FIG. 3 shows a block diagram of the control system 300 of the electrosurgical generator of FIG. 2 in accordance with an embodiment of the present disclosure. The control system 300 includes a summer 302, a PID transfer function 304, a PID coefficient table 306, feedback 308, and a setpoint 310.

In some embodiments, the summer 302, the PID transfer function 304, the PID coefficient table 306, the feedback 308, and the setpoint 310 are implemented by an operative set of processor executable instructions configured to be executed by at least one processor 210 within memory 212 (see FIG. 2). The memory 212 is a non-transitory computer readable (e.g., readable by processor unit 210) medium. In other embodiments, the summer 302, the PID transfer function 304, the PID coefficient table 306, the feedback 308 and the setpoint 310 may be implemented in software, hardware, software in execution, firmware, bytecode, microcode, PLDs, FPGAs, PALs, a microprocessor, a microcontroller, or some combination thereof.

The setpoint 310 may be a target log voltage, log current, log impedance, log power, or the like. Additionally or alternatively, the setpoint 310 may be a target voltage, current, power, or impedance.

The setpoint 310 is provided to summer 302. The summer 302 compares the setpoint 310 to the feedback 308. The setpoint 310 may be a desired or target value, and the feedback 308 provides the actual value being delivered to the load $R_L$ 216.

The feedback 308 corresponds to the setpoint 310. For example, if the setpoint 310 is a target log voltage, then the feedback 308 provides the signal from the amplifier 208, which is the log voltage from load $R_L$ 216.

The feedback 308 may calculate log power by adding the amplified log current signal received from the log amplifier 206 to the amplified log voltage signal received from the log amplifier 208. The feedback 308 may calculate the log impedance by subtracting the log current signal received from the log amplifier 206 from the log voltage signal received from the log amplifier 208. In some embodiments of the present disclosure, the feedback 308 converts an amplified signal from the log amplifiers 206, 208 to an RMS value or an antilog of the amplified sensor signal. In other embodiments of the present disclosure, the feedback 308 does not calculate an antilog from either of the signal from the log amplifiers 206 or the signal from the log amplifier 208. As previously mentioned, the feedback 308 is provided to the summer 302.

The summer 302 compares the setpoint 310 to the feedback 308 and generates an error signal. The error signal is the difference between the setpoint 310 and the feedback 308. Typically, the summer subtracts the feedback from the setpoint 310 (also referred to as negative feedback). The error signal is fed into the PID transfer function 304.

The PID transfer function 304 adds proportional, integral, and derivative terms together and outputs the results to the load $R_L$ 216. Each term includes a coefficient. In some embodiments, the proportional term is the error signal multiplied by a proportional coefficient, the integral term is the integration of the error signal multiplied by an integral coefficient, and the derivative term is the derivative of the error signal multiplied by a derivative coefficient. In some embodiments, the proportional, integral and derivative terms are added together and applied to the load $R_L$ 216. Although FIG. 3 shows the output of the PID transfer function 304 as being directly applied to the load $R_L$ 216, various driver circuitry may be used (e.g., an analog-to-digital converter (not shown), the HVPS 202 and/or the RF output stage 204 as shown in FIG. 2).

The PID coefficients (also referred to as PID gain coefficients) are stored within the PID coefficients table 306. The PID coefficients table 306 provides the PID coefficients to the PID transfer function 304. The PID coefficients table 306 can vary one or more coefficients of the PID transfer function 304 based upon the error signal from the summer 302, a signal from the log amplifiers 206, 208, a log voltage, a log current, a log power, a log impedance, and the like. Additionally or alternatively, the PID coefficients from table 306 may be varied as a function of the voltage, current, power, of the electrosurgical energy as applied to the load $R_L$ 216, or the impedance of the load $R_L$ 216 (e.g., tissue impedance).

In some embodiments, the PID coefficients table 306 may have three ranges for log power with each range having three different PID gain coefficients, and the PID coefficients table 306 may load the PID gain coefficients in accordance with the current power range of the log power.

Figure 4A:
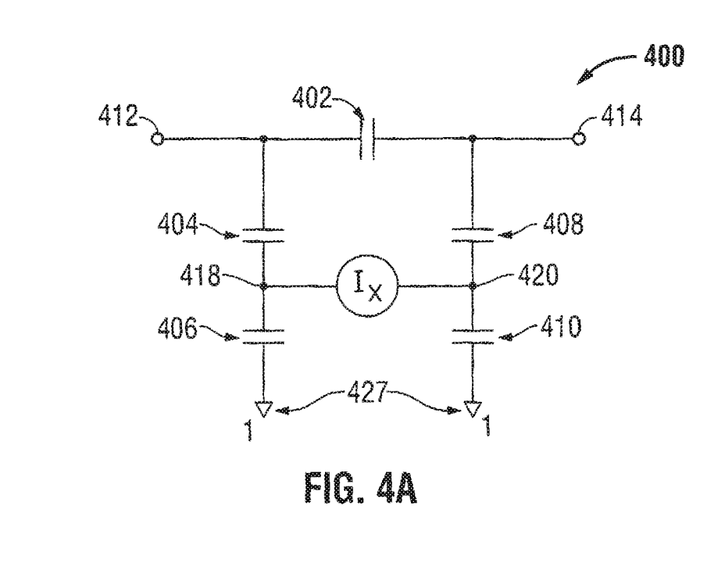
FIG. 4A shows a capacitor divider network for measuring current in accordance with an embodiment of the present disclosure.

FIG. 4A shows a capacitor divider network 400 for measuring current in accordance with an embodiment of the present disclosure. The network 400 includes a configuration of capacitors 402, 404, 406, 408, 410. Referring to FIGS. 2 and 4A, the capacitor 402 is coupled between the nodes 412, 414. The nodes 412, 414 may be coupled between the terminal 104 and ground, respectively, to measure the voltage applied to the load $R_L$ 216. The capacitor 402 is used as a current sense element. As current goes through the capacitor 402, it produces a voltage V, which may be expressed as $$V = \frac{I \cdot dt}{C},$$

where I is the current, dt is the switching time of the RF output stage 428 and C is the capacitance value of the capacitor 402. The capacitor 402 may be used as the low-frequency blocking capacitor for safety standards.

Additionally or alternatively, the nodes 412, 414 may be coupled between the terminals 104, 106, respectively, to measure the current applied to load $R_L$ 216 (see FIG. 2). The current through the capacitor 402 may be derived by measuring the voltage across the capacitor 402 when the capacitance of the capacitor 402 is known or measured.

In some embodiments, as shown in FIG. 4A, the capacitors 402, 404, 406, 408, 410 are arranged in an H configuration and function as a capacitor divider network. The capacitors 404 and 408 are used for isolating the ground of the RF stage 426 from the non-isolated ground 427 of the system. The capacitors 406 and 410 are used to reduce the signal level Ix going to the log amplifier and reference the signal to the system ground 427.

In some embodiments of the present disclosure, optocouplers and/or isolation transformers are used to provide an isolation barrier between the patient and the ground of the generator. The component for sensing current 402 may be the current sensor 218 (FIG. 2). The components for sensing voltage 419, 421, 422, 423 may be the voltage sensor 220 that is electrically coupled to the RF output stage 204. The log amplifier 206 measures the voltage difference between the nodes of: (1) the node 418 between capacitors 404 and 406; and (2) the node 420 between capacitors 408 and 410. The capacitor 402 may be split into various parallel or serial capacitors, e.g., to adjust creepage, clearance, and voltage breakdown for the isolation barrier between the patient and ground. The divider network 400 formed by the capacitors 404, 406, 408, 410 reduces the voltage measured by the log amplifier 206 by a predetermined amount and is a function of the frequency of the electrosurgical energy and the capacitance of the capacitors 402, 404, 406, 408, 410. The capacitors 402, 404, 406, 408, 410 provide isolation between a ground of the electrosurgical generator 102 (see FIG. 2) and the patient P, e.g., to prevent voltage breakdown of the several capacitors 402, 404, 406, 408, 410 during typical use between the patient and a ground of the electrosurgical generator 102.

In some embodiments of the present disclosure, a transformer (not shown) may be interposed between the capacitor 402 and the log amplifier 206 to provide isolation therebetween and/or to step-down the voltage of the electrosurgical energy prior to measurement by the log amplifier 206.

Figure 4B:
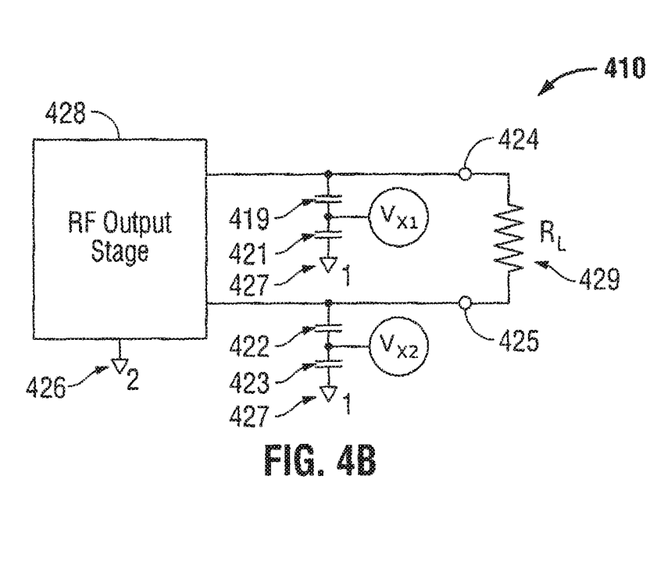
FIG. 4B shows a capacitor divider network for measuring voltage in accordance with an embodiment of the present disclosure.

FIG. 4B shows a capacitor divider network 410 for measuring voltage in accordance with an embodiment of the present disclosure. FIG. 4B shows the isolation of the ground 426 of the RF output stage 428 to the system ground 427 through the capacitors 419 and 422. The capacitors 419 and 422 transfer the voltage across the isolation boundary. The capacitors 421 and 423 reduce the signal level $V_{x1}$ and $V_{x2}$ going to the log amplifier 208 and reference the voltage to system ground 427. The active output 424 of the generator and the return output 425 of the generator are connected to the patient, represented as $R_L$ 429. The two voltages $V_{x1}$ and $V_{x2}$ can fully monitor the output voltage across the patient and serve as redundant sensors.

Figure 5:
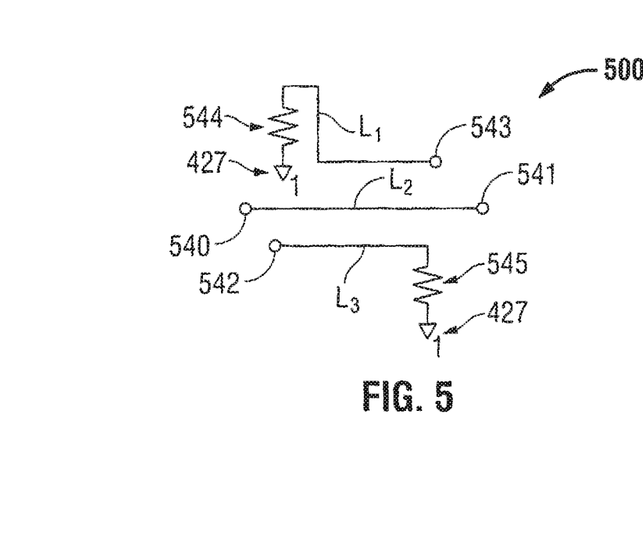
FIG. 5 shows a sensor configuration for a microwave generator in accordance with an embodiment of the present disclosure.

FIG. 5 shows a sensor configuration 500 for a microwave generator in accordance with an embodiment of the present disclosure that provides a dual directional coupler suitable for measurement of forward and reflective voltage. The sensor configuration 500 includes a first line $L_1$ defined between a node 543 and the system ground 427, a second line $L_2$ defined between nodes 541 and 540, and a third line $L_3$ defined between a node 542 and system ground 427

The second line $L_2$ defined between nodes 541 and 540 is connected to a generator. The second line $L_2$ is electromagnetically coupled to the third line $L_3$, which measures the forward voltage and electromagnetically coupled to the first line $L_1$, which measures the reflective voltage. Termination resistors 544 and 545 are provided for the signal lines $L_1$ and $L_3$, respectively. The space between the lines $L_1$ and $L_2$ and the space between the lines $L_2$ and $L_3$ determines the signal strength going to the log amplifier. This signal strength is also influenced by the length of the lines for nodes $L_1$ and $L_2$, the termination resistance 444, 445, and the width of traces for lines $L_1$ and $L_2$.

Figure 6:
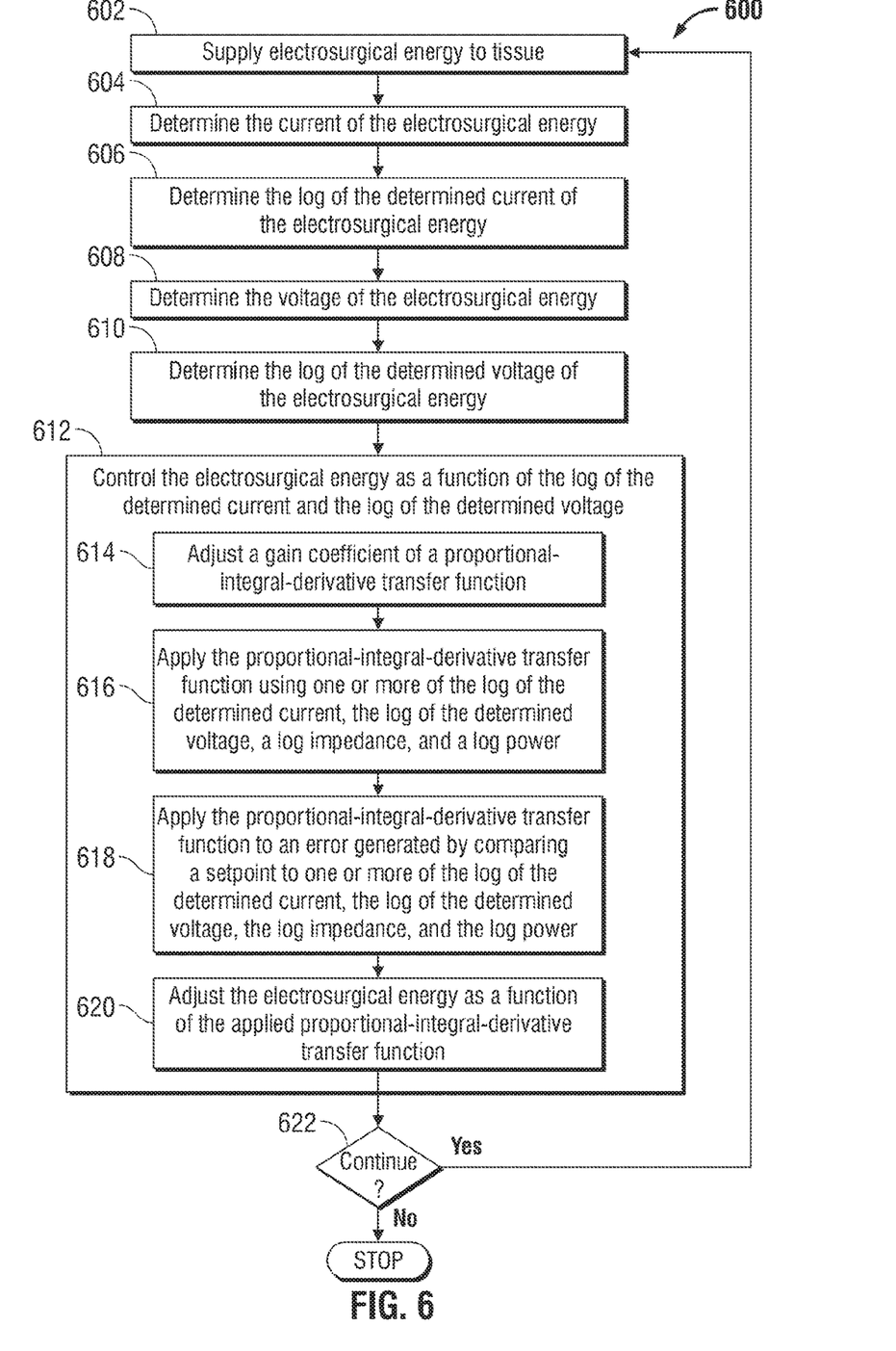
FIG. 6 shows a flow chart diagram of a method for controlling an electrosurgical generator using logarithmic amplifiers in accordance with an embodiment the present disclosure.

FIG. 6 shows a flow chart diagram of a method 600 for controlling an electrosurgical generator using a log amplifier in accordance with an embodiment the present disclosure. Method 600 includes steps 602-620. In step 602, electrosurgical energy is supplied to tissue.

In step 604, the current of the electrosurgical energy is determined. In step 606, the log of the determined current of the electrosurgical energy is determined. For example, step 606 may use the log amplifier 206 of FIG. 2.

In step 608, the voltage of the electrosurgical energy is determined. In step 610, the log of the determined voltage of the electrosurgical energy is determined. Step 608 may use the log amplifier 208 of FIG. 2.

Step 612 includes steps 614 through 620. Step 612 controls the electrosurgical energy as a function of the log of the determined current and the log of the determined voltage. In step 614, a gain coefficient of the proportional-integral-derivative transfer function ("PID transfer function") is adjusted. The PID transfer function of method 600 may be the PID transfer function 304 of FIG. 3. In step 616, a PID transfer function is applied using one or more of the log of the determined current, the log of the determined voltage, a log impedance, and a log power.

In step 618, the PID transfer function is applied to an error generated by comparing a setpoint to one or more of the determined current, the log of the determined voltage, the log impedance, and the log power. Steps 616 and 618 may be integrated together or may be separate.

In step 620, the electrosurgical energy is adjusted as a function of the applied PID transfer function. Thereafter, a manual or automatic deciding step is included in step 622 to determine whether to repeat the method 600 or to stop the application of the electrosurgical energy to tissue. In some embodiments, a pressed button on a portable electrosurgical generator causes the method 600 to repeat until the button is released, then the method 600 will stop; that is, the released button causes method 600 to stop.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A method of controlling an electrosurgical generator, comprising:
    supplying electrosurgical energy to tissue;
    determining a current of the electrosurgical energy;
    determining a log of the determined current of the electrosurgical energy;
    measuring a forward voltage and a reflective voltage of the electrosurgical energy;
    determining a voltage of the electrosurgical energy based on the forward and reflective voltages;
    determining a log of the determined voltage of the electrosurgical energy;
    controlling the electrosurgical energy as a function of the log of the determined current and the log of the determined voltage;
    applying a proportional-integral-derivative transfer function using at least one of the log of the determined current, the log of the determined voltage, a log impedance, or a log power; and
    adjusting the electrosurgical energy as a function of the applied proportional-integral-derivative transfer function.

2. The method according to claim 1, further comprising adjusting a gain coefficient of the proportional-integral-derivative transfer function.

3. The method according to claim 1, wherein the proportional-integral-derivative transfer function is applied to a comparison between a setpoint and at least one of the log of the determined current, the log of the determined voltage, the log impedance, or the log power between a setpoint and at least one of the log of the determined current, the log of the determined voltage, the log impedance, or and the log power.

4. The method according to claim 3, further comprising:
    generating an output log impedance signal by subtracting the current log signal from the voltage log signal; and
    wherein the electrosurgical energy is controlled based on the output log impedance signal.

5. The method according to claim 4, further comprising:
    summing a setpoint and a negation of the output impedance signal to generate an error; and
    wherein the electrosurgical energy is controlled based on a function of the error.

6. The method according to claim 1, wherein the applied proportional-integral-derivative transfer function varies a proportional gain coefficient, an integral gain coefficient and a derivative gain coefficient.

* * * * *